US012171978B2

(12) United States Patent
Kiminami et al.

(10) Patent No.: US 12,171,978 B2
(45) Date of Patent: Dec. 24, 2024

(54) MEDICAL CONTAINER FOR ACCOMMODATING PROTEIN SOLUTION FORMULATION

(71) Applicant: TERUMO KABUSHIKI KAISHA, Tokyo (JP)

(72) Inventors: Hideaki Kiminami, Kanagawa (JP); Koji Nakamura, Tokyo (JP); Yoshihiko Abe, Kanagawa (JP); Shigeru Suzuki, Kanagawa (JP); Shigeru Tamatsukuri, Tokyo (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/470,828

(22) Filed: Mar. 27, 2017

(65) Prior Publication Data

US 2017/0197024 A1 Jul. 13, 2017

Related U.S. Application Data

(63) Continuation of application No. PCT/JP2015/072633, filed on Aug. 10, 2015.

(30) Foreign Application Priority Data

Oct. 2, 2014 (JP) .................................. 2014-203616

(51) Int. Cl.
*A61K 38/16* (2006.01)
*A61J 1/00* (2023.01)
(Continued)

(52) U.S. Cl.
CPC ................ *A61M 5/002* (2013.01); *A61J 1/00* (2013.01); *A61J 1/05* (2013.01); *A61J 1/10* (2013.01);
(Continued)

(58) Field of Classification Search
CPC ...... A61M 5/002; A61M 5/31511; A61J 1/00; A61J 1/05; A61J 1/14; B65D 75/326
See application file for complete search history.

(56) References Cited

U.S. PATENT DOCUMENTS 3,004,679 A * 10/1961 Steierman ............... C03C 17/02
215/49
4,936,314 A * 6/1990 Kasai .................. A61B 5/15003
206/438
(Continued)

FOREIGN PATENT DOCUMENTS

CN 1777406 A 5/2006
CN 1777407 A 5/2006
(Continued)

OTHER PUBLICATIONS

Koji Nakamura, "A Strategy for the Prevention of Protein Oxidation by Drug Product in Polymer-Based Syringes" PDA J Pharm Sci and Tech 2015, 69 88-95.*
(Continued)

*Primary Examiner* — Gideon R Weinerth
(74) *Attorney, Agent, or Firm* — Foley & Lardner LLP

(57) ABSTRACT

A medical container for accommodating a protein solution formulation, in which the medical container is formed from a cycloolefin polymer, sterilized with high-pressure steam, and suppresses oxidization of amino acid residues in a protein in a protein solution formulation accommodated in the medical container.

17 Claims, 1 Drawing Sheet

(51) Int. Cl.
  *A61J 1/05* (2006.01)
  *A61J 1/10* (2006.01)
  *A61J 1/14* (2023.01)
  *A61K 9/08* (2006.01)
  *A61K 38/00* (2006.01)
  *A61K 38/18* (2006.01)
  *A61K 39/395* (2006.01)
  *A61L 2/07* (2006.01)
  *A61M 5/00* (2006.01)
  *A61M 5/31* (2006.01)
  *B65D 75/32* (2006.01)

(52) U.S. Cl.
  CPC .................................... *A61J 1/14* (2013.01); *A61K 9/08* (2013.01); *A61K 38/00* (2013.01); *A61K 38/1816* (2013.01); *A61K 39/395* (2013.01); *A61L 2/07* (2013.01); *B65D 75/326* (2013.01); *A61L 2202/23* (2013.01)

(56) References Cited

U.S. PATENT DOCUMENTS

| | | | | |
|---|---|---|---|---|
| 4,998,400 | A * | 3/1991 | Suzuki | A61J 1/1462 426/124 |
| 5,362,442 | A * | 11/1994 | Kent | A61L 2/0035 204/158.21 |
| 5,610,253 | A * | 3/1997 | Hatke | C08F 232/00 526/160 |
| 5,842,326 | A * | 12/1998 | Wolf | A61L 2/0023 53/425 |
| 6,065,270 | A * | 5/2000 | Reinhard | B65B 3/003 53/140 |
| 6,161,364 | A * | 12/2000 | Kolberg | A61L 2/04 141/18 |
| 6,613,036 | B1 * | 9/2003 | Farmer | A61J 1/10 206/438 |
| 6,688,468 | B2 * | 2/2004 | Waterman | A61J 1/00 206/524.1 |
| 6,912,800 | B2 * | 7/2005 | Vetter | A61L 2/0011 34/209 |
| 7,253,142 | B1 * | 8/2007 | Suzuki | A61K 9/0019 514/20.9 |
| 8,580,192 | B2 * | 11/2013 | Comolli | A61L 2/0035 422/22 |
| 8,727,117 | B2 * | 5/2014 | Maasarani | A61M 5/002 206/364 |
| 9,656,016 | B2 * | 5/2017 | Amarchinta | A61M 5/002 |
| 10,065,784 | B2 * | 9/2018 | Tanoguchi | B01D 53/04 |
| 10,086,148 | B2 * | 10/2018 | Fukushi | A61M 5/3202 |
| 10,246,582 | B2 * | 4/2019 | Sawaguchi | C08L 45/00 |
| 2002/0081401 | A1 * | 6/2002 | Hessok | A61J 1/00 428/34.1 |
| 2002/0150644 | A1 * | 10/2002 | Hetzler | A61L 2/07 425/149 |
| 2002/0153511 | A1 * | 10/2002 | Cotterman | B65B 55/08 252/397 |
| 2002/0172615 | A1 * | 11/2002 | Woodworth | A61L 2/087 422/22 |
| 2003/0034264 | A1 * | 2/2003 | Hamai | A61L 2/04 206/364 |
| 2003/0170410 | A1 | 9/2003 | Buch-Rasmussen et al. | |
| 2005/0129569 | A1 * | 6/2005 | Zhao | A61L 2/081 422/22 |
| 2005/0137368 | A1 * | 6/2005 | Weng | C08F 210/06 526/170 |
| 2005/0171310 | A1 * | 8/2005 | Oshima | C08F 8/04 526/282 |
| 2007/0293441 | A1 | 12/2007 | Choo et al. | |
| 2010/0320215 | A1 * | 12/2010 | Ozaki | A61K 31/4152 220/660 |
| 2011/0060290 | A1 * | 3/2011 | Bonk | A61K 9/0019 604/181 |
| 2012/0123345 | A1 * | 5/2012 | Felts | A61M 5/3129 604/187 |
| 2013/0296235 | A1 * | 11/2013 | Alarcon | A61M 5/3129 514/5.9 |
| 2014/0262883 | A1 * | 9/2014 | Devouassoux | A61M 5/002 206/364 |
| 2015/0224263 | A1 * | 8/2015 | Dugand | B29C 45/14622 604/218 |
| 2015/0273133 | A1 * | 10/2015 | Kerschbaumer | A61M 5/002 206/365 |
| 2016/0058663 | A1 * | 3/2016 | Kumar | A61M 5/14 206/232 |
| 2018/0036310 | A1 * | 2/2018 | Kumar | A61K 31/519 |
| 2018/0169347 | A1 * | 6/2018 | Fukushi | A61M 5/3202 |
| 2018/0221564 | A1 * | 8/2018 | Patel | A61L 2/07 |
| 2018/0264198 | A1 * | 9/2018 | Okihara | A61M 5/3134 |
| 2018/0318513 | A1 * | 11/2018 | Maruyama | A61K 38/00 |
| 2019/0015598 | A1 * | 1/2019 | Takemoto | A61J 1/05 |
| 2019/0022325 | A1 * | 1/2019 | Maruyama | A61K 38/00 |
| 2019/0070072 | A1 * | 3/2019 | Arakawa | A61J 1/05 |
| 2020/0023117 | A1 * | 1/2020 | Maruyama | B65B 3/003 |
| 2022/0313554 | A1 * | 10/2022 | Kiminami | C08F 293/00 |

FOREIGN PATENT DOCUMENTS

| | | |
|---|---|---|
| CN | 101180026 A | 5/2008 |
| CN | 102202643 A | 9/2011 |
| JP | 54910 A | 1/1993 |
| JP | 532277 A | 2/1993 |
| JP | 2001-506887 A | 5/2001 |
| JP | 2003-113112 A | 4/2003 |
| JP | 2007-505712 A | 3/2007 |
| JP | 2009-285318 A | 12/2009 |
| JP | 2011-162267 A | 8/2011 |
| JP | 2012-210315 A | 11/2012 |
| JP | 2013-163017 A | 8/2013 |
| JP | 2014-51502 A | 3/2014 |
| WO | WO-00/15241 A1 | 3/2000 |
| WO | WO-01/17542 A1 | 3/2001 |

OTHER PUBLICATIONS

Hideaki Kiminami "Impact of Sterilization Method on Protein Aggregation and Particle Formation in Polymer-Based Syringes" Journal of Pharmaceutical Sciences 106 (2017) 1001-1007.*

Hideaki Kiminami "Electron beam sterilization of cyclo olefin polymer leads to polymer degradation and production of alkyl radicals" J. Appl. Polym. Sci. 2016.*

William Dierick "Ready to Use Prefillable Syringes: Sterilization Effects on Biopharmaceuticals." Terumo Pharmaceutical Solutions. www.ondrugdelivery.com.*

Harrell, Djonov. "Risks of Using Sterilization by Gamma Radiation: The Other Side of the Coin." International journal of medical sciences 15.3 (2018): 274-279. Web. (Year: 2018).*

Plastics in Medical Devices (Third Edition) Vinny R. Sastri, Material Requirements for Plastics Used in Medical Devices, Editor(s): Vinny R. Sastri, In Plastics Design Library, https://www.sciencedirect.com/science/article/pii/B9780323851268000084 (Year: 2022).*

Introduction to Cyclo Olefin Polymer (COP)—Key Properties Update. S. Suzuki, T. Katayama, K. Arai, T. Sawaguch, Zeon Corporation https://www.zeonex.com/downloads/2016_PDA-1_general_properties_ver.1.pdf (Year: 2016).*

Apel (TM) Cyclo Olefin Copolymer. Mitsui Chemicals Europe https://eu.mitsuichemicals.com/service/product/apel.htm (Year: 2022).*

Shintani H. Formation and elution of toxic compounds from sterilized medical products: methylenedianiline formation in polyurethane. J Biomater Appl. Jul. 1995; 10. (Year: 1995).*

International Search Report issued in International Patent Application No. PCT/JP2015/072633 mailed Sep. 15, 2015.

JP Office Action issued in the corresponding Japanese Patent Application Ser. No. 2016-551615, dated May 31, 2019.

Office Action dated Jan. 15, 2020 in Chinese Patent Application No. 201580053896.2.

(56) References Cited

OTHER PUBLICATIONS

Office Action and Search Report dated Sep. 1, 2020 in corresponding Chinese Patent Application No. 201580053896.2.
Office Action dated Aug. 18, 2020 in corresponding Japanese Patent Application No. 2019-199084.

* cited by examiner

MEDICAL CONTAINER FOR ACCOMMODATING PROTEIN SOLUTION FORMULATION

CROSS-REFERENCE TO RELATED APPLICATIONS

The present application is a bypass continuation of PCT/JP2015/072633, filed on Aug. 10, 2015, which claims priority to Japanese Application No. 2014-203616, filed on Oct. 2, 2014. These applications are hereby incorporated by reference in their entireties.

BACKGROUND

The present disclosure relates to a medical container for accommodating a protein solution formulation, a packed protein solution formulation in which a protein solution formulation is accommodated in the medical container, a packaged product in which the packed protein solution formulation is packaged in a substantially oxygen-impermeable packaging material, and a packaged product in which the packaged product is further packaged in a packaging material having a light-blocking property.

Conventionally and widely used is a packed protein solution formulation in which physiologically active erythropoietin, granulocyte colony stimulating factor, insulin, a monoclonal antibody or another protein formulation in the form of a liquid is accommodated in a container (such as a syringe).

In the packed protein solution formulation, it is necessary that the container accommodating the protein solution formulation does not cause denaturation of a protein, the protein is not adhered to the container, and thus the protein is stably maintained.

In the medical field, recently, a plastic container, which is light, is not easily damaged, and has an excellent handling property, is widely used in place of a glass medical container, which is heavy and breakable.

Examples of plastic materials for producing the medical container include polypropylene, polyethylene, cycloolefin polymer, polyvinyl chloride, polyester, polyamide, polycarbonate, and polymethacrylate.

Among these plastics, cycloolefin polymer is excellent in transparency, heat resistance, radiation-proof sterilization, resistance to acids and alkalis, low dissolution, low impurity, low drug adsorption. Accordingly, it has recently received attention as a material for a medical container and its use is variously attempted. The protein solution formulation is no exception.

Conventionally, known configurations of a protein solution formulation accommodated in a cycloolefin polymer-made container include a packed protein solution formulation in which a protein solution formulation (such as erythropoietin or granulocyte colony stimulating factor) is accommodated in the cycloolefin polymer-made container (WO 01/017542 A and JP 2014-51502 A), and a packed protein solution formulation in which an insulin solution or the like is accommodated in the cycloolefin polymer-made container (JP 2001-506887 A).

In the packed protein solution formulation, a container that accommodates the protein solution formulation needs to be sterilized. Because protein is clotted or denatured by heating, it cannot be heat-sterilized with high-pressure steam after the protein solution formulation is accommodated in the container. Therefore, in the packed protein solution formulation, the container is sterilized before being filled with an aseptically prepared protein solution formulation. A method of irradiating with radioactive rays such as γ rays or electron rays is usually used as the method of sterilizing the container before filling.

SUMMARY

The medical container according to embodiments of the present disclosure can suppress oxidization of amino acid residues in a protein contained in the protein solution formulation accommodated in the container, polymerization of the protein, and anionization of the protein so that denaturation of the protein can be prevented.

Based on the above conventional technology, the present inventors sterilized a cycloolefin polymer-made container by irradiation with electron rays, i.e., a kind of radioactive ray, accommodated the protein solution formulation in the sterilized cycloolefin polymer-made container to prepare a packed protein solution formulation, and examined the stability of the protein in the formulation. It is determined that denaturation of a protein, including the oxidization of amino acid residues in the protein, polymerization of the protein, and anionization of the protein, occurs. The denaturation of a protein, including the oxidization of amino acid residues (such as methionine, cysteine, lysine, and arginine residues) in the protein, polymerization of the protein, and anionization of the protein, may lead to a decrease or elimination of protein's original physiological activity, which is not preferable.

Further, the present inventors sterilized a cycloolefin polymer-made container by irradiation with electron rays, i.e., a kind of radioactive ray, and measured the radical content in the cycloolefin polymer forming the container using an electron spin resonance spectrometer. A high radical content was shown. The present inventors have considered that, if the cycloolefin polymer-made container sterilized by irradiation with electron rays is stored under aseptic conditions for a long period, the radical content in the cycloolefin polymer is decreased. The cycloolefin polymer-made container irradiated with electron rays was stored at room temperature under aseptic conditions for 6 months. After storage for 1 month, the radical content was largely decreased. After storage for 6 months, the radical content was decreased to one thousandth of the content immediately after irradiation with electron rays. Then, the present inventors accommodated the protein solution formulation in the cycloolefin polymer-made container sterilized by irradiation with electron rays and stored to decrease the radical content, and then performed a storage test. Regardless of the fact that the radical content in the cycloolefin polymer was significantly decreased, a significant proportion of the methionine residues in the protein was unexpectedly oxidized. In this regard, among amino acid residues constituting the protein, the methionine residues particularly tend to be oxidized.

Therefore, an object of the present disclosure is to provide a sterilized cycloolefin polymer-made medical container for accommodating a protein solution formulation, which does not cause the denaturation of a protein, particularly denaturation of a protein, including the oxidization of amino acid residues in the protein, even if the protein solution formulation is accommodated and stored.

Another object of the present disclosure is to provide a packed protein solution formulation in which a protein solution formulation is accommodated in a sterile cycloolefin polymer-made container that does not cause denaturation of a protein contained in the protein solution formulation, including the oxidization of amino acid residues in the protein.

Further, another object of the present disclosure is to provide a packaged product that is excellent in long-term storage stability, in which the packed protein solution formulation is packaged in a packaging material.

The present inventors have dedicated repeated studies to achieve the above objects. As a result, the present inventors have found that, in place of the conventional technology of sterilizing a cycloolefin polymer-made container for accommodating a protein solution formulation by irradiating with radioactive rays such as γ rays or electron rays, the cycloolefin polymer-made container is sterilized with high-pressure steam and the protein solution formulation is accommodated in the sterilized container thus obtained, whereby the denaturation of the protein, including the oxidization of amino acid residues in the protein accommodated in the container, is largely reduced, and the denaturation of the protein is suppressed.

Further, the present inventors have found that the cycloolefin polymer-made container sterilized with high-pressure steam has a low radical content of a predetermined value or less, as measured using the electron spin resonance spectrometer.

Further, the present inventors have found the following fact. The protein solution formulation is accommodated in the thus obtained cycloolefin polymer-made container after being sterilized with high-pressure steam, and the protein solution formulation and a deoxygenating agent are packaged in a substantially oxygen-impermeable packaging material so as to form a deoxygenated packaged product, whereby the denaturation caused by the oxidization of amino acid residues in the protein can be prevented by the sterilized container. Furthermore, the oxygen contained in the protein solution formulation, the oxygen contained in the cycloolefin polymer-made container, and the oxygen present between the cycloolefin polymer-made container and the packaging material are absorbed and removed by the deoxygenating agent, whereby the deterioration in quality or deactivation of the protein solution formulation is prevented. Thus, a packaged product of a packed protein solution formulation that is excellent in long-term storage stability is obtained.

The present inventors have also found that the use of the packaging material having a light-blocking property for the deoxygenated packaged product prevents not only the deterioration in quality or deactivation of the protein solution formulation accommodated in the cycloolefin polymer-made container that is caused by oxygen, but also the deterioration in quality or deactivation of the protein solution formulation that is caused by light, and the long-term storage stability becomes more excellent. Thus, the present inventors have developed the present invention based on the above findings.

Incidentally, it is reported that when a cycloolefin-made container sterilized with steam is filled with an aqueous solution composition of calcitonin, i.e., a peptide hormone with 32 amino acids bonded thereto, the remaining percentage of calcitonin is increased, compared to when a cycloolefin-made container sterilized by irradiation with γ rays is filled with an aqueous solution composition of calcitonin (JP 2003-113112 A).

However, JP 2003-113112 A does not describe oxidization of amino acid residues in calcitonin accommodated in the cycloolefin-made container. Further, JP 2003-113112 A does not describe that the cycloolefin-made container sterilized with steam is filled with the aqueous solution composition of calcitonin, whereby oxidization of amino acid residues in calcitonin is reduced, compared to when the cycloolefin-made container sterilized by irradiation with γ rays is filled with the aqueous solution composition of calcitonin.

Further, JP 2003-113112 A does not describe the radical content in the steam-sterilized cycloolefin-made container in which the aqueous solution composition of calcitonin is filled.

Accordingly, embodiments of the present invention include:

(1) a medical container for accommodating a protein solution formulation, wherein the medical container is formed from a cycloolefin polymer, sterilized with high-pressure steam, and suppresses oxidization of amino acid residues in a protein in a protein solution formulation accommodated in the medical container;

(2) a medical container for accommodating a protein solution formulation, wherein the medical container is formed from a cycloolefin polymer, sterilized with high-pressure steam, and has a radical content of $2.2 \times 10^{15}$ radical/g or less as measured using an electron spin resonance spectrometer; and (3) a medical container for accommodating a protein solution formulation, wherein the medical container is formed from a cycloolefin polymer, sterilized with high-pressure steam, and has a radical content of $2.2 \times 10^{15}$ radical/g or less as measured using an electron spin resonance spectrometer, and suppresses oxidization of amino acid residues in a protein in a protein solution formulation accommodated in the medical container.

Further, aspects of the present invention include:

(4) the medical container according to any one of (1) to (3), wherein the medical container is formed from a hydrogenated ring-opened polymer of cycloolefin; and (5) the medical container according to any one of (1) to (4), wherein the medical container is a syringe or cartridge.

In addition, aspects of the present invention include:

(6) a packed protein solution formulation, wherein the protein solution formulation is accommodated in the medical container according to any one of (1) to (5);

(7) the packed protein solution formulation according to (6), wherein the protein solution formulation is a solution formulation of a molecularly targeted drug containing a protein having methionine or cysteine residues in the amino acid sequence;

(8) the packed protein solution formulation according to (6) or (7), wherein the protein solution formulation is a solution formulation of erythropoietin or a monoclonal antibody; and (9) the packed protein solution formulation according to any one of (6) to (8), wherein the packed protein solution formulation is a prefilled syringe.

Moreover, aspects of the present invention include:

(10) a packaged product, wherein the packed protein solution formulation according to anyone of (6) to (9) and a deoxygenating agent are sealed and packaged in a substantially oxygen-impermeable packaging material;

(11) the packaged product according to (10), wherein the oxygen absorption capacity of the deoxygenating agent is one-fifth or more of the volume of the whole storage space of the packaging material;

(12) the packaged product according to (10) or (11), wherein the packaged product is in a blister packaged form; and

(13) the packaged product according to any one of (10) to (12), wherein the substantially oxygen-impermeable packaging material forming the packaged product further has a light-blocking property or the packaged product including the packed protein solution formulation and the deoxygenating agent packaged in the substantially oxygen-impermeable packaging material is further packaged in an outer packaging material having a light-blocking property.

A cycloolefin polymer-made medical container of certain embodiments of the present invention, after being sterilized with high-pressure steam instead of being sterilized by irradiation with radioactive rays, is effective as a container for accommodating the protein solution formulation, because when the protein solution formulation is accommodated in the container, the oxidization of amino acid residues (such as methionine residues) in a protein hardly occurs and the denaturation of the protein can be prevented.

The cycloolefin polymer-made medical container according to certain embodiments of the present invention after being sterilized with high-pressure steam has a low radical content of a predetermined value or less, as measured using the electron spin resonance spectrometer. When the protein solution formulation is accommodated in the container, the oxidization of amino acid residues (such as methionine residues) in a protein hardly occurs and the denaturation of the protein can be prevented. Accordingly, the medical container is effective as a container for accommodating the protein solution formulation.

A packed protein solution formulation of certain embodiments of the present invention is a protein solution formulation accommodated in the cycloolefin polymer-made medical container above, being sterilized with high-pressure steam. Consequently, the denaturation of a protein, including the oxidization of amino acid residues (such as methionine residues) in a protein in the protein solution formulation, barely occurs, and high quality is maintained.

The whole of a packaged product of certain embodiments of the present invention, in which the packed protein solution formulation and a deoxygenating agent are packaged in a substantially oxygen-impermeable packaging material, is maintained under low-oxygen conditions in such a manner that the oxygen contained in the protein solution formulation accommodated in the cycloolefin polymer-made container and the oxygen present in the space of the cycloolefin polymer-made container are absorbed into the deoxygenating agent through the wall of the cycloolefin polymer-made container, and the oxygen present in the space between the cycloolefin polymer-made container and the packaging material is absorbed by the deoxygenating agent. Thus, the packaged product of certain embodiments of the present invention is excellent in long-term storage stability, because the use of the cycloolefin polymer-made container sterilized with high-pressure steam results in prevention of the oxidization of amino acid residues (such as methionine residues) in a protein contained in the protein solution formulation, prevention of the polymerization of the protein, and prevention of the anionization of the protein, which is combined with the oxygen absorbing effect by the deoxygenating agent, and thus the deterioration in quality or deactivation of the protein solution formulation is prevented more effectively.

The packaged product of certain embodiments of the present invention, in which the packed protein solution formulation and a deoxygenating agent are packaged in a substantially oxygen-impermeable packaging material and the resulting packaged product is further packaged in a packaging material having a light-blocking property, is more excellent in long-term storage stability because the oxidization of amino acid residues (such as methionine residues) in a protein contained in the protein solution formulation, the polymerization of the protein, and the anionization of the protein are further suppressed, and the deterioration in quality or deactivation of the protein solution formulation is prevented more effectively.

DETAILED DESCRIPTION

Figure 1:
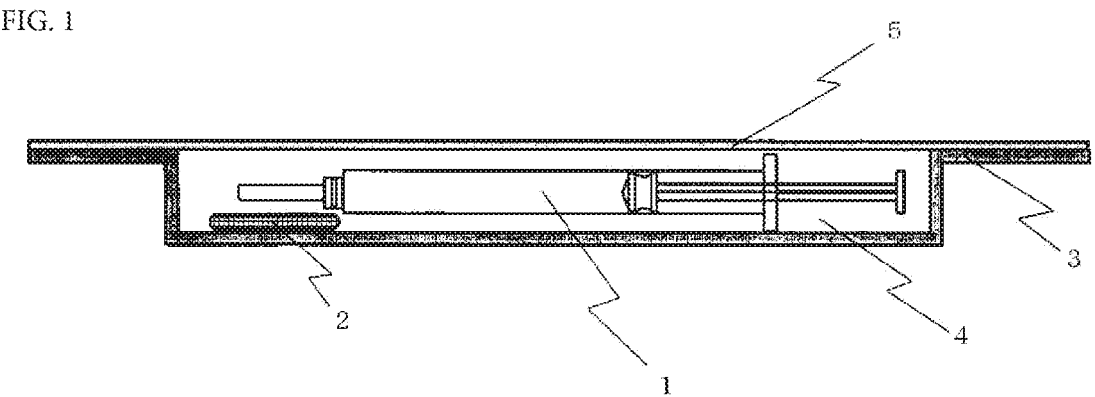
FIG. 1 is a view showing an example of a packaged product according to one embodiment in which a packed protein solution formulation and a deoxygenating agent are sealed and packaged in a substantially oxygen-impermeable packaging material.

Hereinafter, the embodiments of present invention will be described in detail.

The medical container of one embodiment of the present invention, which accommodates a protein solution formulation (medical container before accommodating the protein solution formulation), is formed from a cycloolefin polymer.

The cycloolefin polymer forming the medical container of the may be any polymer as long as it is a cycloolefin polymer which is conventionally known to be used for production of the medical container.

It is preferable that the medical container is formed using one kind or two or more kinds of (a) a ring-opened polymer of cycloolefin (COP), (b) a hydrogenated ring-opened polymer of cycloolefin (COP), and (c) a copolymer of cycloolefin and non-cycloolefin (COC).

The cycloolefin constituting the cycloolefin polymers described in (a) to (c) may be a monocyclic cycloolefin, a polycyclic cycloolefin, a polycyclic cycloolefin having a cross-linked structure, or these may be used in combination thereof. Preferable examples of the cycloolefin include substituted or unsubstituted norbornene monomers, substituted or unsubstituted tetracyclododecen monomers, substituted or unsubstituted dicyclopentadiene monomers, and cyclic polyolefins having cyclohexyl or phenyl group in its side chain.

Examples of the non-cycloolefin constituting the cycloolefin copolymer (COC) described in (c) include ethylene, propylene, butene, isobutylene, and methylpentene, and one kind or two or more kinds of these can be used.

Typical examples of the ring-opened polymer of cycloolefin (COP) described in (a), include, but not limited to, ring-opened polymers of substituted or unsubstituted norbornene, ring-opened polymers of substituted or unsubstituted dicyclopentadiene, ring-opened polymers of substituted or unsubstituted tetracyclododecen, and ring-opened copolymers of substituted or unsubstituted dicyclopentadiene and substituted or unsubstituted tetracyclododecen.

Typical examples of the hydrogenated ring-opened polymer of cycloolefin (COP) described in (b), include, but not limited to, hydrogenated ring-opened polymers of substituted or unsubstituted norbornene, hydrogenated ring-opened polymers of substituted or unsubstituted dicyclopentadiene, hydrogenated ring-opened polymers of substituted or unsubstituted teracyclododecen, and hydrogenated ring-opened polymers of substituted or unsubstituted dicyclopentadiene and substituted or unsubstituted tetracyclododecen.

Typical examples of the copolymer of cycloolefin and non-cycloolefin (COC) described in (c), include, but not limited to, copolymers of substituted or unsubstituted norbornene and ethylene or other non-cycloolefins, copolymers of substituted or unsubstituted tetracyclododecen and ethylene or other non-cycloolefins, and copolymers of cycloolefin having cyclohexyl or phenyl group in its side chain and ethylene or other non-cycloolefins.

Examples of specific products corresponding to the cycloolefin polymers (COP) described in (a) and (b) include "ZEONEX" (registered trademark, manufactured by ZEON CORPORATION) and "ZEONOR" (registered trademark, manufactured by ZEON CORPORATION).

Examples of specific products corresponding to the cycloolefin copolymer (COC) described in (c) include "APEL" (registered trademark, manufactured by Mitsui Chemicals, Inc.) and "TOPAS" (registered trademark," manufactured by Polyplastics Co., Ltd.).

The medical container may be formed from any of cycloolefin polymers.

Among them, the hydrogenated ring-opened polymer of cycloolefin (COP) is preferably used for the medical container. The hydrogenated ring-opened polymer of cycloolefin (COP) does not include a carbon-carbon double bond in its main chain. Thus, radicals are hardly generated in the polymer, whereby oxidization and denaturation of proteins can be further prevented.

The medical container may be independently formed from a cycloolefin polymer. The medical container may have a laminated structure formed from a cycloolefin polymer layer forming an innermost layer of the container and another polymer layer as long as it can withstand a high temperature during sterilization with high-pressure steam. Alternatively, the medical container may be formed from a mixed material of a cycloolefin polymer and another polymer within a range so as not to deviate from the essence of the present invention.

Further, the container body is formed from a cycloolefin polymer depending on the kind of the medical container. The plug, the gasket, the plunger, and other portions may be formed from an elastic body, another plastic, metal, or another material depending on the characteristics to be demanded.

The kind, shape, and size of the medical container are not particularly limited, and they may be selected according to the kind, application, and administration of the protein solution formulation accommodated in the medical container.

The medical container may be, for example, in the form of a syringe (syringe barrel), cartridge (used for a pen-type injection device or the like), vial, bottle, or bag.

Among them, the form of a syringe (syringe barrel) or cartridge is preferred for the medical container. In the case of the medical container in such a form, it is possible to administer the accommodated protein solution formulation without being transferred to another medical device. Thus, the denaturation of the protein during administration can be suppressed.

The medical container may be, for example, a container having an internal volume of 0.5 mL to 5 L.

The cycloolefin polymer-made medical container is sterilized with high-pressure steam before being accommodated in a container for the protein solution formulation.

The temperature and pressure of the high-pressure steam sterilization process may vary depending on the kind of the cycloolefin polymer forming the container, the shape of the container, the kind of the container, the size of the container, the thickness of the container wall, and the like. In order to a complete sterilization in short time while preventing the deformation of the medical container and the deterioration and degradation of the cycloolefin polymer forming the medical container, generally, the heating temperature is preferably from 115 to 134° C., more preferably from 120 to 125° C., and still more preferably from 121 to 123° C.

The time required for the high-pressure steam sterilization process may vary depending on the kind of the cycloolefin polymer forming the container, the shape of the container, the kind of the container, the size of the container, the thickness of the container wall, and the like. Generally, it is preferably from 15 to 60 minutes, more preferably from 15 to 30 minutes, and still more preferably from 20 to 30 minutes.

In the cycloolefin polymer-made container of this embodiment of present invention, after being sterilized with high-pressure steam, the radical content of the cycloolefin polymer forming the container as measured using the electron spin resonance spectrometer is preferably $2.2 \times 10^{15}$/g or less, more preferably $2.0 \times 10^{15}$/g or less, and still more preferably $1.8 \times 10^{15}$/g or less.

The term "radical content as measured using the electron spin resonance spectrometer" used herein means a radical content which is measured using the electron spin resonance spectrometer in accordance with the methods described in "Bell. System. Tech. J." 36, p. 449-484 (1957); and H. M. Swartz H. M., "Biological Application of Electron Spin Resonance", p. 121 (1972). The detailed measurement method is as described in the following examples.

The medical container, sterilized with high-pressure steam, is used as the container for accommodating the protein solution formulation. From this point, the scope of the present invention encompasses the packed protein solution formulation in which the protein solution formulation is previously accommodated in the medical container.

As the protein solution formulation accommodated in the medical container, solution formulations of proteins having and used in the medical field are preferably used. Among them, a solution formulation of a physiologically-active protein having one or both of methionine and cysteine residues, particularly the methionine residue, in the amino acid sequence constituting the protein, is preferably used.

Examples of the protein solution formulation preferably used include, but not limited to, solution formulations which contain hematopoietic factors such as erythropoietin, granulocyte colony-stimulating factors, granulocyte macrophage colony-stimulating factors, and thrombopoietin; molecularly targeted drugs such as monoclonal antibodies, cytokines, antagonists, and agonists; and proteins such as serum albumin, tissue plasminogen activators, insulin, stem cell growth factors, interferon, and interleukin.

Among amino acid residues constituting the protein, the methionine residues particularly tend to be oxidized. The cysteine residues form a disulfide bridge in a molecule or between molecules by oxidization, thereby affecting the higher-order structure of protein. Accordingly, the medical container is suitable as a container for accommodating a solution formulation that contains a protein having methionine or cysteine residues in the amino acid sequence, such as erythropoietin, abatacept, etanercept, adalimumab, rituximab, trastuzumab, or palivizumab.

Further, the higher-order structures of the molecularly targeted drugs including proteins such as monoclonal antibodies, antagonists, and agonists are particularly important in order to exert the effects as drugs. Thus, the medical container is particularly suitable as a container for accommodating a solution formulation that contains a molecularly targeted drug including a protein having methionine or cysteine residues in the amino acid sequence, such as erythropoietin, abatacept, etanercept, adalimumab, rituximab, trastuzumab, or palivizumab.

The blending content, pH, and other physical properties of the protein solution formulation accommodated in the medical container are not particularly limited, and may be set to the blending content and physical properties which are conventionally used in each protein solution formulation, depending on the kind of the protein solution formulation.

The protein solution formulation accommodated in the medical container may contain one kind or two or more kinds of stabilizers, buffers, solubilizing agents, isotonizing agents, pH-modifiers, soothing agents, reducing agents, antioxidants or other components, if necessary.

Examples of the stabilizer which may be contained in the protein solution formulation include nonionic surfactants (sorbitan fatty acid esters, glycerin fatty acid esters, polyglycerin fatty acid esters, polyoxyethylene sorbitan fatty acid esters, polyoxyethylene sorbitol fatty acid esters, polyoxyethylene glycerin fatty acid esters, polyethylene glycol fatty acid esters, polyoxyethylene alkyl ethers, polyoxyethylene polyoxypropylene alkyl ethers, polyoxyethylene alkyl phenyl ethers, polyoxyethylene hardened castor oils, polyoxyethylene beeswax derivatives, polyoxyethylene lanolin derivatives, polyoxyethylene fatty acid amides, lecithin, glycerophospholipids, sphingophospholipids, sucrose fatty acid esters), surfactants such as anionic surfactants (alkyl sulfates, polyoxyethylene alkyl ether sulfates, alkyl sulfosuccinic acid ester salts or the like); and amino acids.

Especially preferred are polyoxyethylene sorbitan fatty acid esters, particularly polyoxyethylene sorbitan monooleate (Polysorbate 80) and/or polyoxyethylene sorbitan monolaurate (Polysorbate 20).

Specific examples of the amino acid to be used as the stabilizer include leucine, tryptophan, serine, glutamic acid, arginine, histidine, lysine, methionine, phenylalanine, acetyl tryptophan, and salts thereof. The amino acid may be in the L-form, D-form, or DL-form.

Among them, L-leucin, L-tryptophan, L-glutamic acid, L-arginine, L-histidine, L-lysine, and salts thereof are preferably used.

Examples of the buffer include phosphates such as sodium monohydrogen phosphate and sodium dihydrogen phosphate; and citrates such as sodium citrate.

Examples of the solubilizing agent include polyoxyethylene sorbitan monooleate (Polysorbate 80) and/or polyoxyethylene sorbitan monolaurate (Polysorbate 20), Cremophor, ethanol, and sodium dodecylbenzene sulfonate.

Examples of the isotonizing agent include polyethylene glycol; and saccharides such as dextran, mannitol, sorbitol, inositol, glucose, fructose, lactose, xylose, mannose, maltose, sucrose, and raffinose.

The protein content in the protein solution formulation accommodated in the medical container is not particularly limited and may be adjusted according to the kind of protein, the application of the protein solution formulation, and the usage form.

Further, the protein solution formulation, which is distributed and sold on the market, is accommodated in the medical container, and may be provided as a packed protein solution formulation.

Examples of the packed protein solution formulation include prefilled syringes, prefilled bag formulations, and prefilled bottle formulations which are distributed and sold on the market in the form in which the protein solution formulation is previously accommodated. Among them, a particularly preferable packed protein solution formulation is a prefilled syringe in which the protein solution formulation is previously accommodated in a syringe or cartridge made from a cycloolefin polymer.

In the case where the packed protein solution formulation is a prefilled syringe or cartridge formulation in which the protein solution formulation is previously accommodated, a prefilled syringe or cartridge containing the protein solution formulation can be obtained by using a syringe or cartridge made from a cycloolefin polymer, which is previously sterilized with high-pressure steam, as a syringe main body (syringe barrel) in the prefilled syringe or a cartridge, attaching or not attaching an injection needle to the end of the syringe barrel, covering the end, filling an aseptically prepared protein solution formulation therein, and sealing by inserting an elastic gasket into the rear end of the syringe barrel or inserting a plunger with the gasket attached thereto.

The packed protein solution formulation that includes the protein solution formulation accommodated in the medical container may be stored, distributed or sold after being packaged in an appropriate packaging material. It is preferable that a packaged product in the form in which the packed protein solution formulation and a deoxygenating agent are sealed and packaged in a substantially oxygen-impermeable packaging material (hereinafter sometimes referred to as "deoxygenated packaged product") is stored, distributed, and sold. The scope of the present invention encompasses the deoxygenated packaged product.

The whole deoxygenated packaged product, including the inside of the protein solution formulation, is maintained under low-oxygen conditions in such a manner that the oxygen present in the space between the cycloolefin polymer-made container and the packaging material is absorbed by the deoxygenating agent, and further the oxygen contained in the protein solution formulation accommodated in the cycloolefin polymer-made container and the oxygen present in the space of the cycloolefin polymer-made container are absorbed into the deoxygenating agent through the wall of the cycloolefin polymer-made container. Accordingly, the deoxygenated packaged product is excellent in long-term storage stability since the use of the cycloolefin polymer-made container sterilized with high-pressure steam results in prevention of the oxidization of amino acid residues in a protein contained in the protein solution formulation, which is combined with the oxygen absorbing effect by the deoxygenating agent, and thus the deterioration in quality or deactivation of the protein solution formulation which is caused by the oxidization is prevented more effectively.

The deoxygenated packaged product, which is packaged in a packaging material having a light-blocking property, is more excellent in long-term storage stability because not only the deterioration in quality or deactivation of the protein solution formulation accommodated in the cycloolefin polymer-made container, which is caused by the oxidization of the protein, but also quality deterioration or deactivation which is caused by light are prevented.

In order to allow the deoxygenated packaged product to have the light-blocking property, for example, (a) a method of seal-packaging a protein solution formulation accommodated in a cycloolefin polymer-made container sterilized with high-pressure steam and a deoxygenating agent using a substantially oxygen-impermeable packaging material having a light-blocking property; or (b) a method of seal-packaging a protein solution formulation accommodated in a cycloolefin polymer-made container sterilized with high-pressure steam and a deoxygenating agent using a substantially oxygen-impermeable packaging material, and further packaging them using an outer packaging material having a light-blocking property; may be used.

As the substantially oxygen-impermeable packaging material used for the deoxygenated packaged product of the present invention, a substantially oxygen-impermeable film or sheet, which is generally widely used, may be used. Examples thereof include a film or sheet formed from polyethylene terephthalate (PET), polyethylenenaphthalate (PEN), ethylene vinyl alcohol copolymer (EVOH), polyvinylidene chloride (PVDC), a vinylidene chloride/vinyl chloride copolymer, a vinylidene chloride/acrylic acid ester copolymer, polyacrylonitrile, polyvinyl alcohol, and polyamide; and a multilayered film or sheet containing at least one of the film or sheet.

Specific examples of the substantially oxygen-impermeable packaging material, include, but not limited to, a multilayered film or sheet having a layer made from a resin such as polyolefin (e.g., polypropylene or polyethylene), polyvinyl chloride, polyester, or polystyrene/polypropylene resin and a layer made from a substantially oxygen-impermeable resin such as polyethylene terephthalate (PET), polyethylenenaphthalate (PEN), an ethylene vinyl alcohol copolymer (EVOH), polyvinylidene chloride (PVDC), a vinylidene chloride-vinyl chloride copolymer, a vinylidene chloride-acrylic acid ester copolymer, polyacrylonitrile, polyvinyl alcohol or polyamide (specific examples thereof include a three-layered film of polypropylene/ethylene-vinyl alcohol copolymer/polypropylene, a three-layered film of polyethylene terephthalate/ethylene-vinyl alcohol copolymer/polypropylene, and a film including a polyethylene terephthalate layer and an ethylene-vinyl alcohol copolymer layer).

Examples of the substantially oxygen-impermeable packaging material having the light-blocking property include a packaging material made from a sheet or film obtained by laminating a layer having a light-blocking property (such as an aluminum foil layer, an aluminum-deposited layer, an oxidized aluminum-deposited layer, or a silicon oxide-deposited layer) on one or both sides of a substantially oxygen-impermeable single-layered film or sheet formed from each of the substantially oxygen-impermeable polymers as listed above; and a packaging material made from a multilayered sheet or film obtained by laminating a layer having a light-blocking property (such as an aluminum foil layer, an aluminum-deposited layer, an oxidized aluminum-deposited layer, or a silicon oxide-deposited layer) on the surface or between layers of the substantially oxygen-impermeable multilayered film or sheet.

Specific examples of the substantially oxygen-impermeable packaging material having the light-blocking property which may be effectively used for the deoxygenated packaged product of the present invention, include, but not limited to, (1) a laminated layer film or sheet having a structure of biaxially stretched polyamide (OPA)/polyethylene (PE)/aluminum-deposited polyethylene terephthalate (PET)/polyethylene (PE);

(2) a laminated layer film or sheet having a structure of OPA/PE/aluminum-deposited PET/PE;

(3) a laminated layer film or sheet having a structure of OPA/PE/aluminum foil/PE/PE;

(4) a laminated layer film or sheet having a structure of OPA/PE/aluminum foil/PE/PET/PE;

(5) a laminated layer film or sheet having a structure of PET/PE/aluminum-deposited PET/PE/ethylene-vinyl acetate copolymer (EVA)/PE;

(6) a laminated layer film or sheet having a structure of polyvinylidene chloride/PE/aluminum-deposited PET/PE; and (7) a laminated layer film or sheet having a structure of PET/aluminum-deposited ethylene-vinylalcohol copolymer (EVOH)/PE.

In the case where the deoxygenated packaged product is packaged using a packaging material having a light-blocking property, separately from a substantially oxygen-impermeable packaging material, examples of the packaging material having a light-blocking property include a sheet or film obtained by forming an aluminum foil layer or an aluminum-deposited layer on aluminum foil, a base sheet or film which is not substantially oxygen-impermeable, a metal container such as a can formed from a metal such as aluminum, and a bag or box container formed from a sheet of paper having a light-blocking property, such as cardboard.

A substantially oxygen-impermeable film or sheet used as the packaging material, a substantially oxygen-impermeable film or sheet having a light-blocking property, or a film or sheet having a light-blocking property which is not substantially oxygen-impermeable may further include an adhesive layer on the surface thereof, the rear surface thereof and/or between layers. Further, printing is performed on the surface thereof, the rear surface thereof, and between layers.

The deoxygenated packaged product may be formed using only one kind of the substantially oxygen-impermeable packaging material or may be formed using two or more kinds of the substantially oxygen-impermeable packaging materials depending on the structure and shape of the packaged product. For example, in the case where the packed protein solution formulation is a prefilled syringe and the prefilled syringe and a deoxygenating agent are packaged by blister packaging, it is possible to allow the blister packaged product to have a structure in which a body portion having a recess for accommodating the prefilled syringe and a covering portion for covering the top surface are formed from a film or sheet which differs from each other and is substantially oxygen-impermeable, or a film or sheet which differs from each other, is substantially oxygen-impermeable, and has a light-blocking property depending on the function required for each portion or the like, after the prefilled syringe is accommodated in the recess, and both portions are sealed at the peripheral edge. In the case where the blister packaged product does not have a light-blocking property, the whole of the blister packaged product may be packaged in the packaging material having a light-blocking property, or may be housed in a container having a light-blocking property.

In the blister packaged product as shown in FIG. 1, a bottom material 3 and a top material 5 are each formed from a film or sheet which is a substantially oxygen-impermeable and has a light-blocking property so that it is possible to produce a blister packaged product which is substantially oxygen-impermeable and has the light-blocking property. Thus, this is preferable. As a result, a deoxygenated packaged product having the light-blocking property can be formed by one packaging without separately using an outer packaging material having a light-blocking property. Additionally, the outer packaging material becomes unnecessary, whereby space-saving is accomplished during storage. Further, the protein solution formulation packed in the cycloolefin polymer container can be easily taken out from the blister packaged product when using.

Further, in the case of the blister packaged product, vibration during transportation is hardly transmitted to the protein solution formulation packed in the cycloolefin polymer container, compared to a packaged product accommodated in a bag. Consequently, the physical stress applied to the protein solution formulation is reduced, and thus the deterioration in quality or deactivation of the protein solution formulation is prevented effectively.

Examples of the blister packaged product which is substantially oxygen-impermeable and has a light-blocking property include, but not limited to, a blister packaged product produced by using any one of the laminated layer sheets described in (1) to (7) as the top material 5 and a polypropylene laminated layer sheet of polypropylene/ethylene vinyl alcohol copolymer (EVOH)/pigment (carbon black etc.) as the bottom material 3.

In the deoxygenated packaged product of the present invention, any deoxygenating agent conventionally used in the medical field may be used as the deoxygenating agent. Examples of the deoxygenating agent which may be used in the present invention include, but not limited to, deoxygenating agents containing iron compounds such as iron hydroxide, iron oxide, and iron carbide as active substances. Examples of commercialized products include AGELESS (registered trademark, manufactured by MITSUBISHI GAS CHEMICAL COMPANY, INC.), MODURAN (registered trademark, manufactured by Nippon Kayaku Co., Ltd.), and SEQUL (registered trademark, manufactured by NISSO FINE CO., LTD.).

The oxygen absorption capacity of the deoxygenating agent is preferably one-fifth or more, more preferably one-third or more, still more preferably 2-fold or more, of the volume of the whole storage space of the deoxygenated packaged product. Accordingly, the whole deoxygenated packaged product, including the inside of the protein solution formulation, is more reliably maintained under low-oxygen conditions, and the deterioration in quality or deactivation of the protein solution formulation which is caused by the oxidization is prevented more effectively.

EXAMPLES

The present invention will be described in more detail with reference to Examples, however the present invention is not limited to the following Examples.

In the following Examples, the radical content of the medical container was calculated as follows.
[Radical Content of Medical Container]

A test specimen of 3 mm×3 mm (length×width) was cut out from the wall of the portion corresponding to the center in the length direction of a medical container [syringe main body (syringe)] and placed in a sample tube having a diameter of about 3.5 mm, and the radical content thereof was measured using an electron spin resonance spectrometer ("ELEXSYS E580", manufactured by Bruker Corporation) under the following conditions. The radical content (radical) per 1 g of the test specimen was calculated.
[Measurement Conditions of Radical Content]
Preset temperature: room temperature (25° C.)
Center magnetic field: near 3517 G
Magnetic field sweep width: 400 G
Modulation: 100 kHz, 2G
Microwave: 9.85 GHz, 0.1 mW
Sweep time: 83.89 s×4 times
Time constant: 163.84 ms
Data point: 1024
Cavity: $TE_{001}$, cylindrical type In Example 1, Comparative Example 1, Reference Example 1, and Examples 2 and 3 described below, the following one was used as the cycloolefin polymer-made medical container.
[Medical Container Made from Cycloolefin Polymer]

A syringe main body having an injection needle for prefilled syringe, which was produced by insert-injection molding using the cyclic polyolefin polymer (COP) (specific gravity: about 1) ("ZEONEX" (registered trademark, manufactured by ZEON CORPORATION)) (syringe size: in accordance with 1 mL-Long in the ISO standard 11040-6, injection needle: 27G)

Production Example 1 Production of Erythropoietin Solution Formulation

Erythropoietin (manufactured by Sigma-Aldrich Co. LLC.) was added to an aqueous solution containing 2 mM $Na_2HPO_4$ and Polysorbate 80 (0.06 mg/mL) and the mixture was completely dissolved to produce a solution (erythropoietin concentration: 24,000 IU/mL). This solution was used as an erythropoietin solution formulation in Example 1, Comparative Example 1, Reference Example 1, and Example 2 described below.

Example 1

(1) Twenty-four syringes (syringe barrels) having needle tips sealed by attaching isoprene rubber caps to the ends of syringe main bodies made from cycloolefin polymer (COP) were placed in an autoclave and sterilized with high-pressure steam at 121° C. for 20 minutes.

(2) The twenty-four syringes sterilized with high-pressure steam in the step (1), were divided into four groups Ia, IIa, IIIa, and IVa six by six.

(3) (i) Six syringes in the first group Ia were further divided into two groups $Ia_1$ and $Ia_2$ three by three.

(ii) From the wall of the portion corresponding to the center in the length direction of the main body of each of the three syringes in the group $Ia_1$ immediately after sterilized with high-pressure steam in the step (1), each test specimen of 3 mm×3 mm (length×width) (weight: about 46 to 61 mg) was cut out, and the radical content thereof was measured by the above method using the electron spin resonance spectrometer. The average of the three specimens was taken to determine the radical content of each syringe main body immediately after sterilized with high-pressure steam.

The results are shown in Table 1 below.

(iii) (a) Three prefilled syringes were prepared by filling 1.0 mL of the erythropoietin solution formulation produced in Production Example 1 in each of the three syringes of the group $Ia_2$, inserting a plunger having a butyl rubber gasket attached to its end into the rear end opening so as to form a 0.2-mL head space, sealing it, allowing the erythropoietin solution formulation to be accommodated in each of the syringes immediately after sterilized with high-pressure steam.

(b) Three prefilled syringes produced in the step (a) were stored at a temperature of 25° C. and a humidity of 60% RH for 4 weeks. After that, the oxidization percentage of methionine residues in the erythropoietin contained in the erythropoietin solution formulation accommodated in the syringe was measured by the following method. The average of the three samples was taken and defined as the oxidization percentage (%) of methionine residues.

The results are shown in Table 1 below.

<Oxidization Percentage of Methionine Residues in Erythropoietin>

(i) A mixture of 100 µL of erythropoietin solution formulation and 400 µL of ammonium acetate (100 mM, pH 8.0) was placed in a receiver of a centrifugal filter ("Amicon Ultra-0.5 10K", manufactured by Milipore Ireland Ltd.) and centrifuged at 14,000 G for 15 minutes.

(ii) The residues on the filter paper were recovered, and an ammonium acetate solution (100 mM, pH 8.0) was added to the recovered residues to give a total amount of 50 µL. To the resulting mixture, 1 µg/mL of Glu-C (pH 5.6) and 100 mM ammonium acetate were added so as to separate oxidized methionine fragments from unoxidized methionine fragments.

(iii) Then, the sample was incubated at 37° C. for 24 hours, diluted with a 10 mM ammonium acetate solution (pH 8.0), and subjected to high-performance liquid chromatography analysis (HPLC) under the following conditions in order to measure the amount of oxidized methionine fragments and the amount of unoxidized methionine fragments.

[Conditions of HPLC]

Mobile phase A: a 0.05% aqueous trifluoroacetic acid solution

Mobile phase B: acetonitrile containing 0.05% of trifluoroacetic acid

Column: octadecyl group-bonded silica gel column (Inertsil ODS-3)

(5 µm, 205 mm×2.1 mm i.d.)

Column temperature: 40° C.,

Injection rate: 30 µL

Total flow rate: 0.25 mL/min

Flow mode: linear gradient mode

Measurement wavelength: 280 nm (iv) On the basis of the amount of oxidized methionine fragments ($Mf_b$) and the amount of unoxidized methionine fragments ($Mf_a$) measured in the step (iii), the oxidization percentage (%) of the methionine residues in the erythropoietin was calculated according to the following Equation <1>.

$$\text{Oxidization percentage of methionine residues (\%)} = \{Mf_b/(Mf_a+Mf_b)\} \times 100 \quad <1>$$

(4) (i) After being sterilized with high-pressure steam in the step (1), six syringes in the second group IIa were stored at a temperature of 25° C. and a humidity of 60% RH for 1 month and further divided into two groups $IIa_1$ and $IIa_2$ three by three.

(ii) From the wall of the portion corresponding to the center in the length direction of the main body of each of the three syringes in the group $IIa_1$ after the storage for 1 month in the step (i), each test specimen of 3 mm×3 mm (length×width) (weight: about 46 to 61 mg) was cut out, and the radical content thereof was measured by the above method using the electron spin resonance spectrometer. The average of the three specimens was taken to determine the radical content of each syringe main body when stored for 1 month immediately after sterilized with high-pressure steam.

The results are shown in Table 1 below.

(iii) (a) Three prefilled syringes were prepared by filling 1.0 mL of the erythropoietin solution formulation produced in Production Example 1 in each of the three syringes of the group $IIa_2$ after being stored for 1 month following the sterilization with high-pressure steam in the step (i), inserting a plunger having a butyl rubber gasket attached to its end into the rear end opening so as to form a 0.2-mL head space, sealing it, allowing the erythropoietin solution formulation to be accommodated in each of the syringes.

(b) Three prefilled syringes produced in the step (a) were stored at a temperature of 25° C. and a humidity of 60% RH for 4 weeks. After that, the oxidization percentage of methionine residues in the erythropoietin contained in the erythropoietin solution formulation accommodated in the syringe was measured by the above method. The average of the three samples was taken and defined as the oxidization percentage (%) of methionine residues.

The results are shown in Table 1 below.

(5) (i) After being sterilized with high-pressure steam in the step (1), six syringes in the third group IIIa were stored at a temperature of 25° C. and a humidity of 60% RH for 3 months and further divided into two groups $IIIa_1$ and $IIIa_2$ three by three.

(ii) From the wall of the portion corresponding to the center in the length direction of the main body of each of the three syringes in the group $IIIa_1$ after the storage for 3 months in the step (i), each test specimen of 3 mm×3 mm (length×width) (weight: about 46 to 61 mg) was cut out and the radical content thereof was measured by the above method using the electron spin resonance spectrometer. The average of the three specimens was taken to determine the radical content of each syringe main body when stored for 3 months immediately after sterilized with high-pressure steam.

The results are shown in Table 1 below.

(iii) (a) Three prefilled syringes were prepared by filling 1.0 mL of the erythropoietin solution formulation produced in Production Example 1 in each of the three syringes of the group $IIIa_2$ after being stored for 3 months following the sterilization with high-pressure steam in the step (i), inserting a plunger having a butyl rubber gasket attached to its end into the rear end opening so as to form a 0.2-mL head space, sealing it, allowing the erythropoietin solution formulation to be accommodated in each of the syringes.

(b) Three prefilled syringes produced in the step (a) were stored at a temperature of 25° C. and a humidity of 60% RH for 4 weeks. After that, the oxidization percentage of methionine residues in the erythropoietin contained in the erythropoietin solution formulation accommodated in the syringe was measured by the above method. The average of the three samples was taken and defined as the oxidization percentage (%) of methionine residues.

The results are shown in Table 1 below.

(6) (i) After sterilized with high-pressure steam in the step (1), six syringes in the fourth group IVa were stored at a temperature of 25° C. and a humidity of 60% RH for 6 months and further divided into two groups $IVa_1$ and $IVa_2$ three by three.

(ii) From the wall of the portion corresponding to the center in the length direction of the main body of each of the three syringes in the group $IVa_1$ after being stored for 6 months following the sterilization with high-pressure steam in the step (i), each test specimen of 3 mm×3 mm (length× width) (weight: about 46 to 61 mg) was cut out and the radical content thereof was measured by the above method using the electron spin resonance spectrometer. The average of the three specimens was taken to determine the radical content of each syringe main body when stored for 6 months immediately after sterilized with high-pressure steam.

The results are shown in Table 1 below.

(iii) (a) Three prefilled syringes were prepared by filling 1.0 mL of the erythropoietin solution formulation produced in Production Example 1 in each of the three syringes of the group IVa$_2$ after being stored for 6 months following the sterilization with high-pressure steam in the step (i), inserting a plunger having a butyl rubber gasket attached to its end into the rear end opening so as to form a 0.2-mL head space, sealing it, allowing the erythropoietin solution formulation to be accommodated in each of the syringes.

(b) Three prefilled syringes produced in the step (a) were stored at a temperature of 25° C. and a humidity of 60% RH for 4 weeks. After that, the oxidization percentage of methionine residues in the erythropoietin contained in the erythropoietin solution formulation accommodated in the syringe was measured by the above method. The average of the three samples was taken and defined as the oxidization percentage (%) of methionine residues.

The results are shown in Table 1 below.

Comparative Example 1

(1) Isoprene rubber caps were attached to the ends of syringe main bodies made from cycloolefin polymer (COP) so as to seal their needle tips, and then twenty-four of the resulting syringes (syringe barrels) were sterilized by irradiation with electron rays of 25 kGy.

(2) Twenty-four syringes sterilized by irradiation with electron rays in the step (1) were divided into four groups Ib, IIb, IIIb, and IVb six by six.

(3) (i) Six syringes in the first group Ib were further divided into two groups Ib$_1$ and Ib$_2$ three by three.

(ii) From the wall of the portion corresponding to the center in the length direction of the main body of each of the three syringes in the group Ib$_1$ immediately after irradiation with electron rays in the step (1), each test specimen of 3 mm×3 mm (length×width) (weight: about 46 to 61 mg) was cut out and the radical content thereof was measured by the above method using the electron spin resonance spectrometer. The average of the three specimens was taken to determine the radical content of each syringe main body immediately after irradiation with electron rays.

The results are shown in Table 1 below.

(iii) (a) Three prefilled syringes were prepared by filling 1.0 mL of the erythropoietin solution formulation produced in Production Example 1 in each of the three syringes of the group Ib$_2$, inserting a plunger having a butyl rubber gasket attached to its end into the rear end opening so as to form a 0.2-mL head space, sealing it, allowing the erythropoietin solution formulation to be accommodated in each of the syringes immediately after irradiation with electron rays.

(b) Three prefilled syringes produced in the step (a) were stored at a temperature of 25° C. and a humidity of 60% RH for 4 weeks. After that, the oxidization percentage of methionine residues in the erythropoietin contained in the erythropoietin solution formulation accommodated in the syringe was measured by the above method. The average of the three samples was taken and defined as the oxidization percentage (%) of methionine residues.

The results are shown in Table 1 below.

(4) (i) After irradiation with electron rays in the step (1), six syringes in the second group IIb were stored at a temperature of 25° C. and a humidity of 60% RH for 1 month and further divided into two groups IIb$_1$ and IIb$_2$ three by three.

(ii) From the wall of the portion corresponding to the center in the length direction of the main body of each of the three syringes in the group IIb$_1$ after being stored for 1 month following irradiation with electron rays in the step (i), each test specimen of 3 mm×3 mm (length×width) (weight: about 46 to 61 mg) was cut out and the radical content thereof was measured by the above method using the electron spin resonance spectrometer. The average of the three specimens was taken to determine the radical content of each syringe main body when stored for 1 month following irradiation with electron rays.

The results are shown in Table 1 below.

(iii) (a) Three prefilled syringes were prepared by filling 1.0 mL of the erythropoietin solution formulation produced in Production Example 1 in each of the three syringes of the group IIb$_2$ after being stored for 1 month in the step (i), inserting a plunger having a butyl rubber gasket attached to its end into the rear end opening so as to form a 0.2-mL head space, sealing it, allowing the erythropoietin solution formulation to be accommodated in each of the syringes.

(b) Three prefilled syringes produced in the step (a) were stored at a temperature of 25° C. and a humidity of 60% RH for 4 weeks. After that, the oxidization percentage of methionine residues in the erythropoietin contained in the erythropoietin solution formulation accommodated in the syringe was measured by the above method. The average of the three samples was taken and defined as the oxidization percentage (%) of methionine residues.

The results are shown in Table 1 below.

(5) (i) After irradiation with electron rays in the step (1), six syringes in the third group IIIb were stored at a temperature of 25° C. and a humidity of 60% RH for 3 months and further divided into two groups IIIb$_1$ and IIIb$_2$ three by three.

(ii) From the wall of the portion corresponding to the center in the length direction of the main body of each of the three syringes in the group IIIb$_1$ after being stored for 3 months following irradiation with electron rays in the step (i), each test specimen of 3 mm×3 mm (length×width) (weight: about 46 to 61 mg) was cut out and the radical content thereof was measured by the above method using the electron spin resonance spectrometer. The average of the three specimens was taken to determine the radical content of each syringe main body when stored for 3 months following irradiation with electron rays.

The results are shown in Table 1 below.

(iii) (a) Three prefilled syringes were prepared by filling 1.0 mL of the erythropoietin solution formulation produced in Production Example 1 in each of the three syringes of the group IIIb$_2$ after being stored for 3 months following irradiation with electron rays in the step (i), inserting a plunger having a butyl rubber gasket attached to its end into the rear end opening so as to form a 0.2-mL head space, sealing it, allowing the erythropoietin solution formulation to be accommodated in each of the syringes.

(b) Three prefilled syringes produced in the step (a) were stored at a temperature of 25° C. and a humidity of 60% RH for 4 weeks. After that, the oxidization percentage of methionine residues in the erythropoietin contained in the erythropoietin solution formulation accommodated in the syringe was measured by the above method. The average of the three samples was taken and defined as the oxidization percentage (%) of methionine residues.

The results are shown in Table 1 below.

(6) (i) After irradiation with electron rays in the step (1), six syringes in the fourth group IVb were stored at a temperature of 25° C. and a humidity of 60% RH for 6 months and further divided into two groups IVb$_1$ and IVb$_2$ three by three.

(ii) From the wall of the portion corresponding to the center in the length direction of the main body of each of the three syringes in the group IVb$_1$ after being stored for 6 months following irradiation with electron rays in the step (i), each test specimen of 3 mm×3 mm (length×width) (weight: about 46 to 61 mg) was cut out and the radical content thereof was measured by the above method using the electron spin resonance spectrometer. The average of the three specimens was taken to determine the radical content of each syringe main body when stored for 6 months following irradiation with electron rays.

The results are shown in Table 1 below.

(iii) (b) Three prefilled syringes were prepared by filling 1.0 mL of the erythropoietin solution formulation produced in Production Example 1 in each of the three syringes of the group IVb$_2$ after being stored for 6 months following irradiation with electron rays in the step (i), inserting a plunger having a butyl rubber gasket attached to its end into the rear end opening so as to form a 0.2-mL head space, sealing it, allowing the erythropoietin solution formulation to be accommodated in each of the syringes.

(b) Three prefilled syringes produced in the step (b) were stored at a temperature of 25° C. and a humidity of 60% RH for 4 weeks. After that, the oxidization percentage of methionine residues in the erythropoietin contained in the erythropoietin solution formulation accommodated in the syringe was measured by the above method. The average of the three samples was taken and defined as the oxidization percentage (%) of methionine residues.

The results are shown in Table 1 below.

Reference Example 1

(1) From the wall of the portion corresponding to the center in the length direction of the main body of each of the three syringe main bodies without being sterilized, each test specimen of 3 mm×3 mm (length×width) (weight: about 46 to 61 mg) was cut out and the radical content thereof was measured by the above method using the electron spin resonance spectrometer. The average of the three specimens was taken to determine the radical content of each syringe main body without being sterilized.

The results are shown in Table 1 below.

(2) (i) Three prefilled syringes were prepared by attaching an isoprene rubber cap to the end of each of different three syringe main bodies without being sterilized so as to seal the needle tip, filling 1.0 mL of the erythropoietin solution formulation produced in Production Example 1 in each of the three syringe main bodies without being sterilized, inserting a plunger having a butyl rubber gasket attached to its end into the rear end opening so as to form a 0.2-mL head space, sealing it, allowing the erythropoietin solution formulation to be accommodated in each of the syringes without being sterilized.

(ii) Three prefilled syringes produced in the step (i) were stored at a temperature of 25° C. and a humidity of 60% RH for 4 weeks. After that, the oxidization percentage of methionine residues in the erythropoietin contained in the erythropoietin solution formulation accommodated in the syringe was measured by the above method. The average of the three samples was taken and defined as the oxidization percentage (%) of methionine residues.

The results are shown in Table 1 below.

TABLE 1

|  | Example 1 | Comparative Example 1 | Reference Example 1 |
|---|---|---|---|
| Sterilization process | Sterilization with high-pressure steam (at 121° C. for 20 minutes) | Irradiation with electron rays (25 kGy) | Not performed |
| Radical content of the syringe main body (radical/g) |  |  |  |
| Immediately after sterilization | $1.5 \times 10^{15}$ | $2.0 \times 10^{18}$ | $1.6 \times 10^{15}$ [1) |
| After storage for 1 month | $1.6 \times 10^{15}$ | $8.4 \times 10^{15}$ |  |
| After storage for 3 months | $1.5 \times 10^{15}$ | $3.9 \times 10^{15}$ |  |
| After storage for 6 months | $1.6 \times 10^{15}$ | $2.5 \times 10^{15}$ |  |
| Oxidization percentage of methionine residues in erythropoietin (%) |  |  |  |
| Accommodated in a syringe immediately after sterilization | 5.0 | 13.2 | 6.0 [2) |
| Accommodated in a syringe stored for 1 month after sterilization | 3.1 | 9.1 |  |
| Accommodated in a syringe stored for 3 months after sterilization | 3.2 | 7.4 |  |
| Accommodated in a syringe stored for 6 months after sterilization | 3.7 | 9.4 |  |

[1) Radical content of an unsterilized syringe main body

[2) Oxidization percentage of methionine residues when the erythropoietin solution formulation was accommodated in the unsterilized syringe and stored at a temperature of 25° C. and a humidity of 60% RH for 4 weeks As apparent from the results in Table 1 above, the oxidization percentage of the methionine residues in the protein (erythropoietin) contained in the solution formulation was small when the protein (erythropoietin) solution formulation was accommodated in the cycloolefin polymer-made medical container (syringe) of Example 1 after being sterilized with high-pressure steam and stored. Thus, the denaturation of the protein can be suppressed.

On the other hand, when the protein (erythropoietin) solution formulation was accommodated in the cycloolefin polymer-made container of Comparative Example 1 after being sterilized by irradiation with electron rays and stored, the oxidization percentage of the methionine residues in the protein (erythropoietin) contained in the solution formulation was 2-fold or more of Example 1. Thus, the denaturation of the protein easily occurs.

Additionally, when the cycloolefin polymer-made container of Comparative Example 1 sterilized by irradiation with electron rays is left, for example, for 6 months after sterilization by irradiation with electron rays, the radical content in the cycloolefin polymer is decreased to one-hundredth or less of that after irradiation with electron rays. Nevertheless, in the case where the protein (erythropoietin) solution formulation is accommodated in the cycloolefin polymer-made container after being left for 6 months, the oxidization percentage of the methionine residues in the protein (erythropoietin) contained in the solution formulation is still high. Thus, the oxidization denaturation of the protein easily occurs.

Example 2

(1) (i) A three-layered film of polypropylene (195 μm)/ethylene-vinylalcohol copolymer (10 μm)/polypropylene (195 μm) was used as the bottom material 3 to form a recess 4 for accommodating a prefilled syringe 1 having the erythropoietin solution formulation accommodated therein and a deoxygenating agent 2 in the bottom material 3 as shown in FIG. 1.

(ii) Both the deoxygenating agent 2 ["AGELESS (registered trademark) Z-10PTR" manufactured by MITSUBISHI GAS CHEMICAL COMPANY, INC.] and the prefilled syringe 1 having the erythropoietin solution formulation accommodated in the syringe after being sterilized with high-pressure steam, which was produced by performing the same operation of (a) of (iii) of (6) of Example 1 (prefilled syringe having the erythropoietin solution formulation accommodated in the syringe main body after being stored at 25° C. for 6 months following the sterilization with high-pressure steam) were accommodated in the recess 4 formed in the step (i).

(iii) Then, the opened top surface was covered with the top material 5 of polyethylene terephthalate (16 μm)/adhesive layer/printing surface/ethylene-vinylalcohol copolymer (12 μm)/adhesive layer/ethylene-vinyl acetate copolymer (30 μm), and the peripheral edge was sealed. Thus, a packaged product of a prefilled syringe having the erythropoietin solution formulation accommodated therein was produced by blister packaging as shown in FIG. 1. In this regard, in the blister packaged product, the volume of the space having the prefilled syringe and the deoxygenating agent accommodated therein was about 27 $cm^3$, and the oxygen absorption capacity of the deoxygenating agent 2 was 10 $cm^3$.

(iv) The blister packaged product obtained in the step (iii) was stored at a temperature of 25° C. and a humidity of 60% RH for 3 months and 6 months. After storage for 3 months and 6 months, the oxidization percentage of the methionine residues in the erythropoietin contained in the erythropoietin solution formulation accommodated in the syringe was measured by the above method, it was as shown in Table 2.

(2) (i) The prefilled syringe having the erythropoietin solution formulation accommodated in the syringe after being sterilized with high-pressure steam (the prefilled syringe having the erythropoietin solution formulation accommodated in the syringe main body after being stored at 25° C. for 6 months following the sterilization with high-pressure steam in the step (i)) (the prefilled syringe which was not subjected to blister packaging) were stored at a temperature of 25° C. and a humidity of 60% RH for 3 months and 6 months. After storage for 3 months and 6 months, the oxidization percentage of the methionine residues in the erythropoietin contained in the erythropoietin solution formulation accommodated in the syringe was measured by the above method, it was as shown in Table 2.

TABLE 2

| | Oxidization percentage of methionine residues in erythropoietin (%) | | |
|---|---|---|---|
| | Start of storage (25° C., 60% RH) | After storage for 3 months (25° C., 60% RH) | After storage for 6 months (25° C., 60% RH) |
| Blister packaged together with the deoxygenating agent | 2.5 | 3.2 | 3.7 |
| Neither the deoxygenating agent nor blister packaging | 2.5 | 4.1 | 5.3 |

As apparent from the results in Table 2 above, the prefilled syringe having the erythropoietin solution formulation accommodated in the syringe made from a cycloolefin polymer sterilized with high-pressure steam and a deoxygenating agent are packaged in a substantially oxygen-impermeable packaging material to form a deoxygenated packaged product, whereby the oxidization percentage of the methionine residues in erythropoietin is further decreased.

[Monoclonal Antibody Solution Formulation]

In Examples 3 and Comparative Example 2 below, a complete human IgG1 monoclonal antibody: adalimumab [product name: Humira (registered trademark) manufactured by Abbive Inc.] was used as the monoclonal antibody solution formulation.

Example 3

(1) Twenty-four syringes (syringe barrels) having needle tips sealed by attaching isoprene rubber caps to the ends of syringe main bodies made from cycloolefin polymer (COP) were placed in an autoclave and sterilized with high-pressure steam at 121° C. for 20 minutes in the same manner as in (1) of Example 1, followed by storage at a temperature of 25° C. and a humidity of 60% RH for 1 month.

(2) Twenty-four monoclonal antibody solution formulation packed in syringes were produced by filling 500 µL of the monoclonal antibody solution formulation in each of the twenty four syringes obtained in the step (1) after being stored for 1 month following the sterilization with high-pressure steam, inserting a plunger having a butyl rubber gasket attached to its end into the rear end opening so as to form a 0.2-mL head space, sealing it, allowing the monoclonal antibody solution formulation to be accommodated in each of the sterilized syringes.

(3) Each of the monoclonal antibody solution formulations packed in the twenty-four syringes obtained in the step (2) and the same deoxygenating agent as that used in Example 2 were blister packaged in a packaging material for blister packaging formed from the same material and structure as those used in Example 2 in the same manner as in Example 2, followed by incubation at 5° C. for 7 days.

Figure 2:
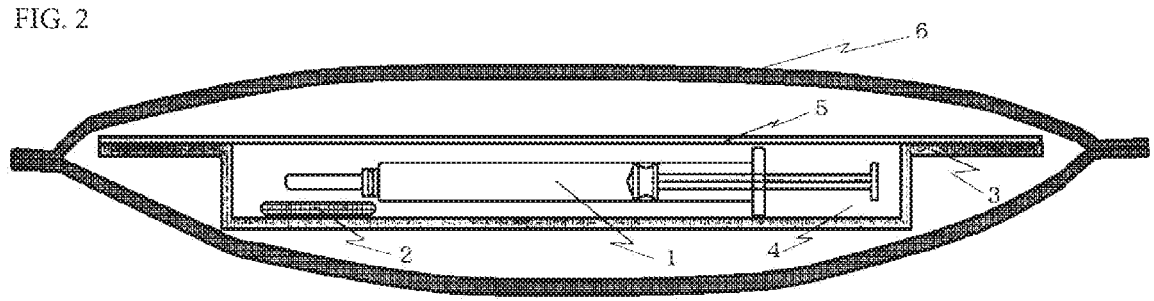
FIG. 2 is a view showing an example of a packaged product according to one embodiment in which a packed protein solution formulation and a deoxygenating agent are sealed and packaged in a substantially oxygen-impermeable packaging material, and which is further packaged in an outer packaging material having a light-blocking property (outer bag).

(4) Twenty-four packaged products after incubation in the step (3) were divided into two groups (group I and group II) twelve by twelve. The twelve packaged products in the group I were left as they were without being placed in an outer bag having a light-blocking property (outer packaging material). As shown in FIG. 2, each of the twelve packaged products in the group II was placed in an outer bag 6 having a light-blocking property (an outer packaging material formed from a laminated layer sheet having a layer structure of biaxially stretched polyamide/polyethylene/aluminum-deposited polyethylene terephthalate/polyethylene) and sealed.

(5) The twelve packaged products in the group I which was not packed in an outer bag and the twelve packaged products of the group II which was packed in the outer bag 6 having the light-blocking property were stored at a temperature of 25° C. for 25 days under irradiation with light (2000 lux). The oxidization percentage of the methionine residues (Met256 and Met432) in the monoclonal antibody contained in the monoclonal antibody solution formulation, the formation percentage of high-molecular weight species, and the formation percentage of acidic molecular species (at the start of storage (on day 0), after storage for 7 days, after storage for 14 days, after storage for 25 days) were calculated by the following method.

In order to calculate the oxidization percentage of methionine residues, the formation percentage of high-molecular weight species, and the formation percentage of acidic molecular species, three of the twelve packaged products in both the groups I and II were measured at the start of storage (before irradiation with light), the other three packaged products were measured after storage for 7 days under irradiation with light, the other three packaged products were measured after storage for 14 days under irradiation with light, and the remained three packaged products were measured after storage for 25 days under irradiation with light. Then, the average of the three packaged products was taken.

The results are shown in Table 3 below.

<Oxidization Percentage of Methionine Residues in Monoclonal Antibody>

The oxidization percentage of the methionine residues in the monoclonal antibody was determined by the peptide mapping method in the following manner.

(i) 100 µg of the sample (monoclonal antibody (IgG1) solution formulation) was denatured with 8M guanidinium chloride. Then, the buffer in the sample was substituted for a digestion buffer (100 mM Tris-HCl buffer, Polysorbate 80 content: 0.02% by mass, pH: 8.0) using MicroSpin G-25 Column (manufactured by General Electric Company (GE Healthcare), United Kingdom).

(ii) 3.2 µg of sequence-grade modified trypsin was added to the sample and the mixture was incubated at 37° C. for 60 minutes so as to be digested. Then, 10 µL of 25% trifluoroacetic acid was added thereto so as to terminate the digestion reaction.

(iii) The digestion peptides were separated by reversed-phase high-performance liquid chromatography (HPLC) using an LC1200 system (Agilent Technologies) employing AdvanceBio Peptide Map 2.1×150 mm, 2.7 µm column under the following conditions.

[Conditions of HPLC]
Mobile phase A: an aqueous solution of water and trifluoroacetic acid at a ratio of 1000:1
Mobile phase B: a mixture of water, acetonitrile, and trifluoroacetic acid at a ratio of 400:3600:3
Column: AdvanceBio Peptide Map (2.1×150 mm, 2.7 µm)
Column temperature: 50° C.,
Injection rate: 30 µL
Flow rate: 0.2 mL/min
Flow mode: linear gradient mode (mobile phase B, from 0% to 45%, exceeding 60 minutes)

(iv) The eluted peptide fraction was detected using LTQ/XL Orbitrap Mass Spectrometer (Thermo Fisher Scientific Inc.) including an electrospray ion source (cation mode; 300 to 2000 m/z value). The oxidization percentage of the methionine residues was quantified using ion chromatograms extracted based on the theoretical m/z of peptides containing Met256 or Met432 (±10 ppm).

<Formation Percentage of High-Molecular Weight Species>>

The formation percentage of high-molecular weight species was determined by molecular sieve chromatography (SEC) as follows:

(i) 250 µL of the sample (monoclonal antibody (IgG1) solution formulation) was supplied to two TSKgel SuperSWmAb HR columns (manufactured by TOSOH CORPORATION) connected in series, and the sample was fractionated for every molecular weight using a phosphate buffer (phosphoric acid: 100 mM, sodium chloride: 400 mM, pH 7.0) at an isocratic flow (flow rate: 0.5 mL/min, temperature: 25° C.) (measurement wavelength: 280 nm).

(ii) The elution peak (fraction) before the main peak corresponds to high-molecular weight species (components having a higher molecular weight than that of the monoclonal antibody), and the elution peak (fraction) after the main peak corresponds to low-molecular weight species (components having a lower molecular weight than that of the monoclonal antibody). The formation percentage (%) of the high-molecular weight species was calculated according to Equation <2> below.

Formation percentage of high-molecular weight species (%)=$(MW_H/MW_T) \times 100$ <2>

(wherein, $MW_H$ represents the total elution peak (fraction) before the main peak, and $MW_T$ represents the total elution peak (all fractions))

<Formation Percentage of Acidic Molecular Species>

The formation percentage of acidic molecular species was calculated by cation-exchange high-performance liquid chromatography (CEX-HPLC) as follows:

(i) 25 μg of the sample (monoclonal antibody (IgG1) solution formulation) was supplied to the Propac WCX-10 Column (manufactured by Thermo Fisher Scientific Inc.), and analyzed by high performance liquid chromatography under the following conditions.

[Conditions of HPLC]
- Mobile phase A: a 20 mM sodium phosphate solution (pH 6.8)
- Mobile phase B: an aqueous solution (pH 6.8) prepared by adding solid sodium chloride to a 20 mM sodium phosphate solution until the sodium chloride concentration reaches 500 mM
- Column: Propac WCX-10 column
- Column temperature: 40° C.,
- Injection rate: 25 μg
- Flow rate: 0.7 mL/min
- Flow mode: linear gradient mode (mobile phase B, from 9% to 18%)
- Measurement wavelength: 280 nm (ii) The elution peak (fraction) before the main peak corresponds to acidic molecular species (components exhibiting anionic properties stronger than those of the monoclonal antibodies), and the elution peak (fraction) after the main peak corresponds to alkaline molecular species (components exhibiting anionic properties weaker than those of the monoclonal antibodies). The formation percentage of acidic molecular species (%) was calculated according to Equation <3> below.

Formation percentage of acidic molecular species (%)=$(A_M/T_M) \times 100$   <3>

(wherein, $A_M$ represents the total elution peak (fraction) before the main peak, and $T_M$ represents the total elution peak (all fractions))

Comparative Example 2

(1) Twelve syringes (syringe barrels) having injection needle tips sealed by attaching isoprene rubber caps to the ends of glass syringe main bodies (syringe size: in accordance with 1 mL-Long in the ISO standard 11040-6, injection needle: 27G) were provided.

(2) Twelve monoclonal antibody solution formulations packed in glass syringes were produced by filling 500 μL of the monoclonal antibody solution formulation in each of the twelve syringes provided in the step (1), inserting a plunger having a butyl rubber gasket attached to its end into the rear end opening so as to form a 0.2-mL head space, sealing it, allowing the monoclonal antibody solution formulation to be accommodated in each of the syringes.

(3) Each of the monoclonal antibody solution formulations packed in the twelve glass syringes obtained in the step (2) and the same deoxygenating agent as that used in Example 2 were blister packaged in a packaging material for blister packaging formed from the same material and structure as those used in Example 2 in the same manner as in Example 2, followed by incubation at 5° C. for 7 days.

(4) Twelve packaged products obtained in the step (3) after incubation (packaged products which was not packed in an outer bag having a light-blocking property) were stored under irradiation with light (2000 lux) at a temperature of 25° C. for 25 days. The oxidization percentage of the methionine residues (Met256 and Met432) in the monoclonal antibody contained in the monoclonal antibody solution formulation, the formation percentage of high-molecular weight species, and the formation percentage of acidic molecular species (at the start of storage (on day 0), after storage for 7 days, after storage for 14 days, after storage for 25 days) were calculated by the above method.

In order to calculate the oxidization percentage of methionine residues, the formation percentage of high-molecular weight species, and the formation percentage of acidic molecular species, three of the twelve packaged products were measured at the start of storage (before irradiation with light), the other three packaged products were measured after storage for 7 days under irradiation with light, the other three packaged products were measured after storage for 14 days under irradiation with light, and the remained three packaged products were measured after storage for 25 days under irradiation with light. Then, the average of the three packaged products was taken.

The results are shown in Table 3 below.

TABLE 3

| | Example 3 | | Comparative |
| --- | --- | --- | --- |
| | Group I | Group II | Example 2 |
| Material of syringe main body | Cycloolefin polymer (COP) | Cycloolefin polymer (COP) | Glass |
| Sterilization with high-pressure steam before filling a monoclonal antibody solution | performed | performed | not performed |
| Storage after sterilization with high-pressure steam before filling a monoclonal antibody solution | at 25° C. and RH 60% for 1 month | at 25° C. and RH 60% for 1 month | not performed |
| Packaging form | Blister packaged in a substantially oxygen-impermeable packaging material, together with a deoxygenating agent | Blister packaged in a substantially oxygen-impermeable packaging material, together with a deoxygenating agent | Blister packaged in a substantially oxygen-impermeable packaging material, together with a deoxygenating agent |

TABLE 3-continued

|  | Example 3 | | Comparative |
|---|---|---|---|
|  | Group I | Group II | Example 2 |
| Packaged with an outer bag having a light-blocking property | not performed | performed | not performed |
| [Oxidization percentage of methionine residues[1)]] | | | |
| Oxidization percentage of Met256 | | | |
| On day 0 | 5% | 4% | 4% |
| After storage for 7 days | 6% | 4% | 7% |
| After storage for 14 days | 8% | 4% | 10% |
| After storage for 25 days | 9% | 4% | 14% |
| Oxidization percentage of Met432 | | | |
| On day 0 | 2% | 2% | 2% |
| After storage for 7 days | 3% | 2% | 3% |
| After storage for 14 days | 4% | 2% | 6% |
| After storage for 25 days | 6% | 2% | 9% |
| [Formation percentage of high-molecular weight species] | | | |
| On day 0 | 1.5% | 1.1% | 1.2% |
| After storage for 7 days | 2.6% | 1.1% | 2.7% |
| After storage for 14 days | 3.9% | 1.1% | 4.8% |
| After storage for 25 days | 5.5% | 1.0% | 7.3% |
| [Formation percentage of acidic molecular species] | | | |
| On day 0 | 17% | 14% | 14% |
| After storage for 7 days | 24% | 16% | 24% |
| After storage for 14 days | 31% | 18% | 34% |
| After storage for 25 days | 39% | 20% | 20% |

[1)]Percentage when stored under irradiation with light (2000 lux) at a temperature of 25° C.

The comparison between the result of the group I of Example 3 and the result of Comparative Example 2 shows the following. In the blister packaged product in the group I of Example 3, a prefilled syringe including a monoclonal antibody solution formulation filled in a syringe main body made from a cycloolefin polymer (COP), which has been stored for a predetermined period after being sterilized with high-pressure steam to decrease the radical content, and a deoxygenating agent are blister packaged in a substantially oxygen-impermeable packaging material. When the blister packaged product is stored in the light, the oxidization percentage of the protein constituting the monoclonal antibody (particularly methionine residues in the protein) is low, the formation percentage of high-molecular weight species is low, and the formation percentage of acidic molecular species is low after storage for 14 days and 25 days, as compared to the blister packaged product of Comparative Example 2 in which a prefilled syringe including a monoclonal antibody solution formulation filled in a glass syringe main body and a deoxygenating agent are blister packaged in a substantially oxygen-impermeable packaging material.

Conventionally, it has been considered that since the cycloolefin polymer container has a higher oxygen permeability than that of a glass container, the cycloolefin polymer container as a container for accommodating proteins such as monoclonal antibodies is inferior to the glass container. The results in Table 3 show the following. In the packaged product in which the protein solution formulation packed in a cycloolefin polymer container, which has been stored for a predetermined period after being sterilized with high-pressure steam to decrease the radical content and which is filled with a solution formulation of a protein (such as a monoclonal antibody), and a deoxygenating agent are packaged in a substantially oxygen-impermeable packaging material, the denaturation of a protein, including the oxidization of the protein solution formulation accommodated in the container, polymerization of the protein, and anionization of the protein is suppressed and excellent storage stability is exhibited, as compared to the packaged product in which the protein solution formulation packed in a glass container filled with a solution formulation of a protein (such as a monoclonal antibody) and a deoxygenating agent are packaged in a substantially oxygen-impermeable packaging material.

The results of the groups I and II of Example 3 in Table 3 will be observed. In the packaged product in the group II of Example 3, the blister packaged product of the group I formed by blister packaging a prefilled syringe including a monoclonal antibody solution formulation filled in a syringe main body made from a cycloolefin polymer (COP) and a deoxygenating agent in a substantially oxygen-impermeable packaging material is further packaged in an outer bag having a light-blocking property. Consequently, the oxidization percentage of the protein constituting the monoclonal antibody (particularly methionine residues in the protein) is very low, the formation percentage of high-molecular weight species is very low, and the formation percentage of acidic molecular species is very low, compared to the packaged product of the group I of Example 3 which is not packaged in the outer bag having the light-blocking property.

The results indicate the following: a packaged product in which a solution formulation of a protein (such as a monoclonal antibody) filled in a cycloolefin polymer container, which has been stored for a predetermined period after being sterilized with high-pressure steam to decrease the radical content, and a deoxygenating agent are packaged in a substantially oxygen-impermeable packaging material, and the deoxygenated packaged product is further packaged in an outer packaging material having a light-blocking property; or a packaged product in which a protein solution formulation packed in a cycloolefin polymer container and a deoxygenating agent are packaged in a packaging material which is substantially oxygen-impermeable and has a light-blocking property are more effective in preventing the denaturation of a protein, including the oxidization of the protein solution formulation accommodated in the container, polymerization of the protein, and anionization of the protein, and in improving long-term storage stability.

A cycloolefin polymer-made medical container after being sterilized with high-pressure steam, has an effect of preventing the oxidization of methionine residues in a protein, and accommodates a protein solution formulation or a cycloolefin polymer-made medical container after being sterilized with high-pressure steam, has a radical content of $2.2 \times 10^{15}$ radical/g or less as measured using the electron spin resonance spectrometer, and accommodates a protein solution formulation can be effectively used as the container for accommodating the protein solution formulation, because when the protein solution formulation is accommodated in the medical container, the oxidization of amino acid residues such as methionine residues in a protein hardly occurs and the denaturation of the protein can be prevented.

A packed protein solution formulation in which the protein solution formulation is accommodated in the medical container is useful as the protein solution formulation because the oxidization of amino acid residues (such as methionine residues) in a protein hardly occurs and the denaturation of the protein can be prevented.

A packaged deoxygenated product in which the packed protein solution formulation and a deoxygenating agent are packaged in a substantially oxygen-impermeable packaging material, is very useful, because the whole packaged product is maintained under low-oxygen conditions, the use of the cycloolefin polymer-made container sterilized with high-pressure steam results in prevention of the oxidization of amino acid residues such as methionine residues in a protein, which is combined with the oxygen absorbing effect by the deoxygenating agent, and thus the deterioration in quality or deactivation of the protein solution formulation which is caused by the oxidization is prevented more effectively, and long-term stable storage is achieved.

Further, as for a packaged product in which a protein solution formulation filled in a cycloolefin polymer container, which has been stored for a predetermined period after being sterilized with high-pressure steam to decrease the radical content, and a deoxygenating agent are packaged in a substantially oxygen-impermeable packaging material, and the deoxygenated packaged product is further packaged in an outer packaging material having a light-blocking property; or a packaged product in which a protein solution formulation packed in a cycloolefin polymer container and a deoxygenating agent are packaged in a packaging material which is substantially oxygen-impermeable and has a light-blocking property, the residual body of the packaged product is maintained under low-oxygen conditions. Accordingly, the use of the cycloolefin polymer-made container sterilized with high-pressure steam results in prevention of the oxidization of amino acid residues (such as methionine residues) in a protein contained in the protein solution formulation, which is combined with the oxygen absorbing effect by the deoxygenating agent and the light blocking effect by the packaging material having the light-blocking property, and the deterioration in quality or deactivation of the protein solution formulation which is caused by oxidization and light is prevented more effectively. Thus, long-term stable storage is achieved, which is very useful.

REFERENCE SIGNS LIST

1 Prefilled syringe containing erythropoietin solution formulation
2 Deoxygenating agent
3 Bottom material
4 Recess
5 Top material
6 Outer bag having a light-blocking property (outer packaging material)

What is claimed is:

1. A product comprising:
   a sterilized medical container that suppresses oxidization of amino acid residues, wherein the medical container consists essentially of a cycloolefin polymer and was sterilized with high-pressure steam; and
   a stable protein solution accommodated in the medical container, wherein the protein solution comprises a protein selected from the group consisting of erythropoietin, a granulocyte colony-stimulating factor, thrombopoietin, a tissue plasminogen activator, a stem cell growth factor, an interferon, and an interleukin, and wherein 5% or less of methionine residues in the protein are oxidized immediately after accommodation in the medical container and for at least 4 weeks thereafter.

2. A product of claim 1,
   wherein the medical container has a radical content of $2.2 \times 10^{15}$ radical/g or less as measured using an electron spin resonance spectrometer.

3. The product of claim 2,
   wherein the medical container suppresses oxidization of amino acid residues in a protein in a protein solution formulation accommodated in the medical container.

4. The product according to claim 1, wherein the cycloolefin polymer is a hydrogenated ring-opened polymer.

5. The product according to claim 2, wherein the cycloolefin polymer is a hydrogenated ring-opened polymer.

6. The product according to claim 3, wherein the cycloolefin polymer is a hydrogenated ring-opened polymer.

7. The product according to claim 1, wherein the medical container is a syringe or cartridge.

8. The product according to claim 2, wherein the medical container is a syringe or cartridge.

9. The product according to claim 3, wherein the medical container is a syringe or cartridge.

10. The product according to claim 4, wherein the medical container is a syringe or cartridge.

11. The product according to claim 1, wherein the protein is erythropoietin.

12. The product according to claim 1, wherein the medical container is a syringe.

13. A packaged product comprising:
    the product of claim 1; and
    a substantially oxygen-impermeable packaging material in which the product is sealed and packaged along with a deoxygenating agent.

14. The packaged product according to claim 13, wherein an oxygen absorption capacity of the deoxygenating agent is one-fifth or more of a volume of a storage space within the packaging material.

15. The packaged product according to claim 13, wherein the packaged product a blister package.

16. The packaged product according to claim 13, wherein the substantially oxygen-impermeable packaging material has a light-blocking property.

17. The packaged product according to claim 13, further comprising an outer packaging material in which the oxygen-impermeable packaging material is contained, the outer packaging material having a light-blocking property.

* * * * *